US010365221B2

(12) United States Patent
Li et al.

(10) Patent No.: US 10,365,221 B2
(45) Date of Patent: Jul. 30, 2019

(54) RAMAN SPECTRUM PLANE IMAGING DEVICE

(71) Applicant: Institute of Materials, China Academy of Engineering Physics, Jiangyou, Mianyang (CN)

(72) Inventors: Haibo Li, Mianyang (CN); Wenhua Luo, Mianyang (CN); Gan Li, Mianyang (CN); Yuejiao Gu, Mianyang (CN); Guangfeng Zhang, Mianyang (CN); Pengfei Yang, Mianyang (CN)

(73) Assignee: Institute of Materials, China Academy of Engineering Physics, Jiangyou, Mianyang (CN)

( * ) Notice: Subject to any disclaimer, the term of this patent is extended or adjusted under 35 U.S.C. 154(b) by 0 days.

(21) Appl. No.: 15/925,596

(22) Filed: Mar. 19, 2018

(65) Prior Publication Data

US 2018/0275064 A1    Sep. 27, 2018

(30) Foreign Application Priority Data

Mar. 21, 2017   (CN) .......................... 2017 1 0168751

(51) Int. Cl.
| | |
|---|---|
| *G01J 3/44* | (2006.01) |
| *G01N 21/65* | (2006.01) |
| *G01N 21/01* | (2006.01) |
| *G01J 3/10* | (2006.01) |
| *G01J 3/26* | (2006.01) |

(Continued)

(52) U.S. Cl.
CPC ................ *G01N 21/65* (2013.01); *G01J 3/10* (2013.01); *G01J 3/26* (2013.01); *G01J 3/2803* (2013.01); *G01J 3/44* (2013.01); *G01N 21/01* (2013.01); *G01J 2003/1213* (2013.01); *G01J 2003/4424* (2013.01); *G01N 2021/656* (2013.01)

(58) Field of Classification Search
CPC ................. G01N 21/65; G01N 21/658; G01N 2021/656; G01J 3/44; G01J 3/02
USPC ....................................................... 356/301
See application file for complete search history.

(56) References Cited

U.S. PATENT DOCUMENTS

2006/0119853 A1*  6/2006  Baumberg ........... G01N 21/658
                                                      356/445
2007/0019209 A1*  1/2007  Pfaff .................... G01R 15/241
                                                      356/511

(Continued)

*Primary Examiner* — Md M Rahman
(74) *Attorney, Agent, or Firm* — Knobbe Martens Olson & Bear LLP

(57) ABSTRACT

Aspects of Raman spectrum plane imaging device(s), belonging to the technical field of Raman spectra, are disclosed. In one example, a Raman spectrum plane imaging device may comprise a laser generation apparatus capable of adjusting an output wavelength, a light filtering apparatus, and a planar array detector. Laser light beams emitted by such laser generation apparatus may irradiate on a surface of a sample in a planar illuminating manner. According to systems herein, Raman scattered light generated by the sample under the excitation of the laser light beams is incident on the light filtering apparatus and is imaged on the planar array detector after selectively passing through the light filtering apparatus, to be received by the planar array detector. In some implementations, the light filtering apparatus may comprise an F-P interference device and a bandpass light filter.

14 Claims, 3 Drawing Sheets

(51) Int. Cl.
*G01J 3/28* (2006.01)
*G01J 3/12* (2006.01)

(56) References Cited

U.S. PATENT DOCUMENTS

| | | | | |
|---|---|---|---|---|
| 2012/0257196 | A1* | 10/2012 | Raicu | G02B 21/002 356/300 |
| 2012/0327417 | A1* | 12/2012 | Amako | G01N 21/658 356/445 |
| 2013/0176562 | A1* | 7/2013 | Shioi | G01J 3/4412 356/301 |
| 2013/0188181 | A1* | 7/2013 | Angel | G01J 3/44 356/301 |
| 2014/0247447 | A1* | 9/2014 | Angel | G01J 3/44 356/301 |
| 2015/0201117 | A1* | 7/2015 | Acher | G01Q 40/00 348/79 |
| 2016/0202124 | A1* | 7/2016 | Lambert | G01J 3/44 356/301 |
| 2016/0289669 | A1* | 10/2016 | Fan | C12Q 1/6874 |

* cited by examiner

RAMAN SPECTRUM PLANE IMAGING DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims benefit/priority of Chinese Patent application No. CN201710168751.8, published as Chinese Patent Publication No. 106645093 A, and filed on Mar. 21, 2017, with the State Intellectual Property Office (SIPO) of the People's Republic of China, which is incorporated herein by reference in entirety.

BACKGROUND

Field

The present disclosure relates to the technical field of Raman spectra, and particularly to a Raman spectrum plane imaging device.

Description of the Related Art

Raman spectroscopy, as a nondestructive fingerprint-type detecting method, has been widely applied to fields of scientific research, production, and in other areas, whereas an image can provide people with intuitive and vivid spatial distribution information. Raman spectrum imaging technology, which integrates the advantages of both spectrum and image, can express the information of spatial distribution of chemical components of a sample through images, which is not only vivid and intuitive, but also completely contains molecular structure information of the sample, particularly suitable for analyzing samples with a micro-nano structure. A conventional Raman spectrometer realizes the Raman spectrum imaging through a detecting manner of exciting one point of a sample with laser light of a fixed wavelength, splitting light by a monochromatic means, and receiving the light by a linear array CCD (Charge-coupled Device), and through point-by-point or line-by-line scanning, which has a low imaging resolution and a slow imaging speed.

The low imaging resolution and the slow imaging speed are bottleneck-type problems preventing broad application of the Raman spectrum imaging technology. The imaging resolution is one of the most important parameters of the imaging technology. An image with low resolution cannot well reflect the real state of the sample. The slow imaging speed (generally tens of minutes, and even tens of hours) has extremely high requirements on the stability of equipment and sample, resulting in that the Raman imaging technology is hardly applied/utilized in practice.

SUMMARY OF CERTAIN ASPECTS

Embodiments of the present disclosure provide a Raman spectrum plane imaging device capable of effectively improving the spatial resolution and the imaging speed of Raman spectrum imaging.

In order to realize objective(s) such as that above, one technical solution consistent with the present disclosure is as follows.

One example of the present disclosure discloses a Raman spectrum plane imaging device, including a laser generation apparatus, a light filtering apparatus, and a planar array detector. Laser light beams emitted by the laser generation apparatus irradiate on a preset region of a surface of a sample in a planar illuminating manner, and further Raman scattered light, generated by the sample under excitation of the laser light beams, is incident on the light filtering apparatus, and is imaged on the planar array detector after selectively passing through the light filtering apparatus, to be received by the planar array detector, wherein an output wavelength of the laser generation apparatus may be adjustable.

Further, the above light filtering apparatus includes a band-pass light filter and a Fabry-Perot (F-P) interference device, wherein the Fabry-Perot interference device is arranged between the band-pass light filter and the planar array detector. The Raman scattered light generated by the sample under excitation of the laser light beams is incident on the band-pass light filter, hence is incident on the Fabry-Perot interference device after selectively passing through the band-pass light filter, and emerges from the Fabry-Perot interference device and then is imaged on the planar array detector, wherein a free spectrum range of the Fabry-Perot interference device is larger than a half of the band-pass width of the band-pass light filter. By arranging the Fabry-Perot interference device on a detecting light path, the spectrum resolution is greatly improved, thus realizing fast Raman spectrum imaging with both high spectrum resolution and spatial resolution. Such implementations may be beneficial to detection of samples with complicated Raman spectra, and/or to exerting the advantage of the fingerprint characteristic of the Raman spectrum.

In some implementations, the above band-pass light filter may be a narrow-band light filter.

In other implementations, an incident angle of the Raman scattered light incident on the narrow-band light filter is adjustable.

In further implementations, the above band-pass light filter may be a band-pass light filter with a fixed central wavelength.

Additionally, the above light filtering apparatus may further include a long-pass light filter, and the Raman scattered light, generated by the sample under the excitation of the laser light beams, may pass through the long-pass light filter, the band-pass light filter, and the Fabry-Perot interference device in sequence, and is then imaged on the planar array detector.

Further, the above laser generation apparatus may include a tunable laser device and/or a beam expander, wherein laser light beams emitted by the tunable laser device, after being expanded by the beam expander, irradiate on the surface of the sample, and the planar illuminating manner may be a Kohler-, critical-, or defocusing-type planar illuminating manner.

In implementations herein, the above Raman spectrum plane imaging device may further include a converging lens and/or an objective lens, wherein the laser light beams emitted by the tunable laser device, after being expanded by the beam expander, passes through the converging lens and the objective lens in sequence, and then irradiate on the surface of the sample.

Further, the above Raman spectrum plane imaging device may further include a dichroscope, wherein the laser light beams emitted by the laser generation apparatus are incident on the dichroscope and reflected by the dichroscope, to irradiate on the preset region of the surface of the sample, and the Raman scattered light, generated by the sample under the excitation of the laser light beams, is incident on the dichroscope, passes through the dichroscope, and then is incident on the light filtering apparatus.

In some implementations, the output wavelength of the above laser generation apparatus can be adjusted continuously.

Compared with the known art, in Raman spectrum plane imaging devices consistent with the present disclosure, the laser light beams output by the laser generation apparatus irradiate on the preset region of the sample in the planar illuminating manner, the generated Raman scattered light, after selectively passing through the light filtering device based on spectra, is imaged on the planar array detector, to directly obtain the Raman spectrum image of the preset region of the surface of the sample. Use of such planar excitation and planar imaging manners effectively improves the imaging speed and the imaging spatial resolution of the Raman spectrum imaging. Further, by adjusting the output wavelength of the laser generation apparatus, the Raman displacement selection and continuous scanning for the sample can be realized without switching the light filtering apparatus. The Raman spectrum plane imaging device is suitable for detecting the Raman spectrum imaging of different substances.

In order to make the objectives, features, and advantages of the present disclosure, such as those above, more apparent and understandable, the following examples are particularly illustrated in combination with the accompanying drawings to provide a detailed description of various illustrative implementations.

BRIEF DESCRIPTION OF THE DRAWINGS

In order to more clearly illustrate technical solutions of examples of the present disclosure, figures which are needed for description of the examples will be introduced briefly below. It should be understood that the figures below merely show some examples of the present disclosure, and therefore should not be considered as limiting the scope. A person of ordinary skill in the art still may obtain other relevant implementations in accordance with these figures and disclosure.

In the figures, the elements corresponding to the various callouts are as follows: 10—Raman spectrum plane imaging device; 110—laser generation apparatus; 111—tunable laser device; 112—beam expander; 113—short-pass light filter; 114—first reflecting mirror; 115—second reflecting mirror; 120—converging lens; 130—dichroscope; 140—objective lens; 150—light filtering apparatus; 151—narrow-band light filter; 152—F-P interference device; 153—long-pass light filter; 160—imaging lens; 170—planar array detector; 20—sample.

DETAILED DESCRIPTION OF ILLUSTRATIVE IMPLEMENTATIONS

Below, technical solutions of the present disclosure are described clearly and completely in conjunction with figures of the present disclosure. It should be apparent that some but not all of the examples of the present disclosure are described. Generally, components in the examples of the present disclosure described and shown in the figures herein may be arranged and designed in various different configurations. Therefore, the detailed description below of the examples of the present disclosure provided in the figures is not intended to limit the scope of protection of the present disclosure, but merely represents chosen examples of the present disclosure. It should be noted that similar callouts and description(s) represent similar items in the following figures, therefore, once a certain item is defined in one figure, it is not needed to be further defined and explained in subsequent figures.

In the description of the present disclosure, it should be noted that orientational or positional relationships indicated by terms such as "center", "upper", "lower", "left", "front", "back", "inner", and "outer" and so on are based on orientational or positional relationships as shown in the figures, or orientational or positional relationships in which the present innovations are conventionally placed, merely for facilitating describing the present disclosure and simplifying the description, rather than indicating or implying that the related devices or elements have to be in the specific orientation or configured and operated in specific orientation, therefore, they should not be construed as limiting the present disclosure. Further, use of terms such as "first" and "second" and so on are merely for descriptive purpose, but should not be construed as indicating or implying importance in relativity.

In the description of the present disclosure, it also should be indicated that unless otherwise expressly specified and defined, term "provided" should be understood in a broad sense. For a person ordinarily skilled in the art, the specific meanings of the above-mentioned terms in the present disclosure can be understood according to specific circumstances.

Figure 1:
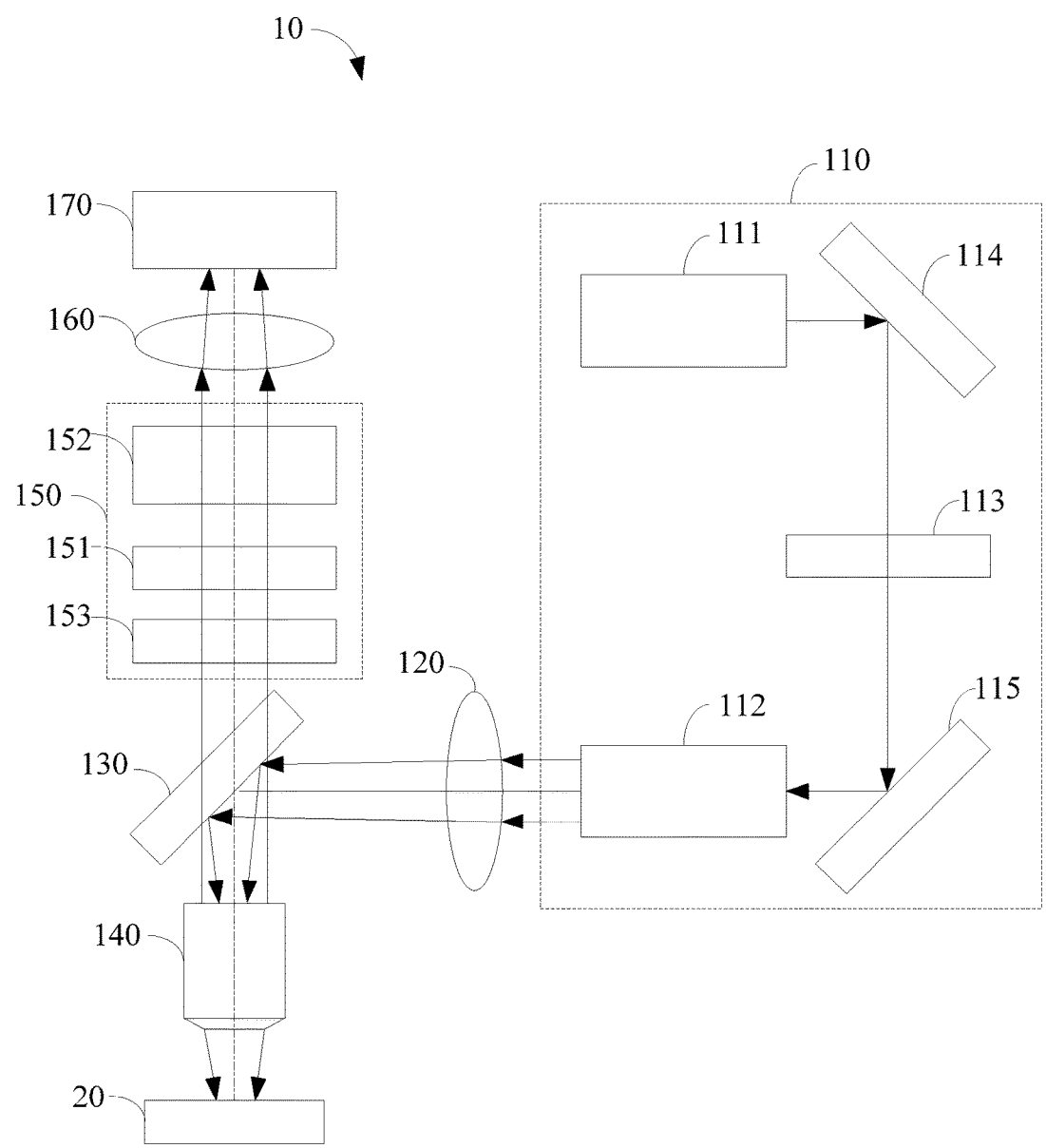
FIG. 1 is a structural schematic view of a Raman spectrum plane imaging device, according to one or more exemplary implementations of the present disclosure.

As shown in FIG. 1, an example of the present disclosure provides a Raman spectrum plane imaging device 10, including a laser generation apparatus 110, a light filtering apparatus 150, and a planar array detector 170. Laser light beams emitted by the laser generation apparatus 110 irradiate on a preset region of a surface of a sample 20 in a planar illuminating manner. Raman scattered light, generated by the sample 20 under the excitation of the laser light beams, is incident on the light filtering apparatus 150, selectively passes through the light filtering apparatus 150 and then is imaged on the planar array detector 170, to be received by the planar array detector 170. It should be indicated that solid lines each having an arrow in FIG. 1 are used for showing transmission directions of light beams.

Different from the conventional Raman spectrometer which excites a certain point or line on the sample 20 through a laser with a fixed wavelength, in exemplary implementations of the present disclosure, the laser light beams emitted by the laser generation apparatus 110 irradiate on the preset region of the surface of the sample 20, wherein a specific area of the preset region, i.e., an area of field of view of the present Raman spectrum plane imaging device 10 can be designed as required. For example, this preset region may be a square region or a circular region. In the present example, such excitation manner is defined as a plane excitation manner, and in combination with the planar array detector 170, a Raman spectrum image of the preset region of the surface of the sample 20 may be directly obtained, effectively improving the imaging speed and the imaging spatial resolution of the Raman spectrum imaging.

Consistent with the present examples, the laser generation apparatus 110 may be used for outputting excited light, of which an output wavelength is adjustable. In some implementations, its output wavelength can be adjusted continuously. Specifically, the laser generation apparatus 110 can include a tunable laser device 111, wherein the tunable laser device 111 may be, but not limited to, any one of dye laser device, semiconductor laser device, Ti sapphire laser device, excimer laser device and other wavelength tunable laser devices 111 with continuous output or pulsed output.

In order to increase the diameter of the laser light beams emitted by the tunable laser device 111, the laser generation apparatus 110 further includes a beam expander 112 for expanding the laser light beams emitted by the tunable laser device 111.

In order to prevent a fluorescent background and the like from affecting the Raman imaging effect, the above laser generation apparatus 110 may further include a short-pass light filter 113, wherein the laser emitted by the tunable laser device 111 is filtered by the short-pass light filter 113 to eliminate stray light such as fluorescent background that affects the Raman imaging. For example, the short-pass light filter 113 may be arranged between the tunable laser device 111 and the beam expander 112.

Taking the reasonability of the spatial layout of the laser generation apparatus 110 into consideration, the laser generation apparatus 110 may further include a first reflecting mirror 114 and a second reflecting mirror 115, as shown in FIG. 1. The laser emitted by the tunable laser device 111 is reflected by the first reflecting mirror 114 and the second reflecting mirror 115 to the beam expander 112, at this time, the above short-pass light filter 113 may be arranged in a light propagating path between the first reflecting mirror 114 and the second reflecting mirror 115.

In order to enable the expanded laser light beams to uniformly irradiate on the sample 20, as shown in FIG. 1, the present Raman spectrum plane imaging device 10 may further include a converging lens 120 and an objective lens 140. The laser light beams emitted by the tunable laser device 111, after being expanded by the beam expander 112, are incident on the converging lens 120. The converging lens 120 projects the incident laser light beams onto a rear focal plane of the objective lens 140, so that the laser light uniformly irradiates on the surface of the sample 20. The energy of the excited light irradiating on the sample 20 is distributed uniformly, being beneficial to Raman imaging. Of course, in addition to the above Kohler illuminating manner realized with the converging lens 120 and the objective lens 140, other planar illuminating manners may also be used in the present example to enable the laser light beams to irradiate on the sample 20, for example, planar illuminating manner of an optical fiber illuminating type, critical illuminating type or defocus type.

Based on the above contents, in the present example, through an excited light path formed by the beam expander 112, the converging lens 120, and the objective lens 140, the laser light beams emitted by the tunable laser device 111 can be uniformly incident on the surface of the sample 20, and a Raman signal generated by the sample 20 under excitation is imaged onto the planar array detector 170 and received by the planar array detector 170.

According to one or more implementations herein, the receiving light path of Raman scattered light and the above excited light path may be independent from each other, or may also share some elements. In one example of the present disclosure, in order to optimize the light path structure of the device, the receiving light path and the excited light path may use the objective lens 140 in common. At this time, the present Raman spectrum plane imaging device may further include a dichroscope 130. The dichroscope 130, serving a function of reflecting the laser light beams and transmitting the Raman scattered light, may enable the receiving light path and the excited light path to use the objective lens 140 in common to respectively realize excitation and detection. That is, by providing the dichroscope 130, an optical axis of the excited light path and an optical axis of the receiving light path are overlapped. As shown in FIG. 1, the expanded laser light beams, after passing through the converging lens 120, are incident on the dichroscope 130 and reflected by the dichroscope 130, pass through the objective lens 140 and irradiate on the surface of the sample 20. A part of the Raman scattered light, generated by the sample 20 under the excitation of the laser light beams, passes through the objective lens 140, and then is incident on the dichroscope 130. The Raman scattered light transmitted through the dichroscope 130 is filtered by the light filtering apparatus 150 and then imaged on the planar array detector 170.

In order to make it easy to add a filtering component in the receiving light path, an infinite imaging manner is advantageously used in the present disclosure, that is, after a part of the scattered light (including Rayleigh scattered light and Raman scattered light), formed by the laser light beams incident on the sample 20, is incident on the objective lens 140, the part of the scattered light is collimated by the objective lens 140 into parallel light to emerge, passes through the dichroscope 130 and the light filtering apparatus 150, and then is imaged on the planar array detector 170 and received by the planar array detector 170. When the parallel light beams emerging through the objective lens 140 have a relatively large diameter which is incompatible with the dimension of the planar array detector 170, an imaging lens 160 can be arranged in the light path between the light filtering device 150 and the planar array detector 170, so that the image obtained through the objective lens 140 is zoomed out by the imaging lens 160 to an appropriate dimension, and then is imaged on the planar array detector 170.

In the present example, the light filtering apparatus 150 is arranged in the receiving light path, for filtering out light, other than light having Raman characteristic peak, generated by the sample 20 under the effect of the incident laser light beams, such as Rayleigh scattered background light, to selectively transmit light which has Raman characteristic peak at a specific central wavelength, so as to realize the Raman spectrum imaging. Specifically, the light filtering apparatus 150 at least includes a band-pass light filter. In the present example, the band-pass light filter can be a band-pass light filter with a fixed central wavelength, and the light having the Raman characteristic peak at this central wavelength may be transmitted through the band-pass light filter and imaged on the planar array detector 170.

In order to improve the spectrum resolution of the Raman spectrum imaging, the above band-pass light filter may be or include a narrow-band light filter 151. In order to be able to realize the fine tuning of the central wavelength of the narrow-band light filter 151, for example, an incident angle of the Raman scattered light incident on the narrow-band light filter 151 is adjustable. By adjusting the incident angle of the Raman scattered angle incident on the band-pass light filter, a peak wavelength of a transmission peak of the narrow-band light filter 151 is finely tuned, so as to obtain more precise Raman spectrum information. For example, the incident angle of the light beams incident on the narrow-band light filter 151 can be adjusted by adjusting the angle of the narrow-band light filter 151.

Due to the limitation of the band-pass width of the narrow-band light filter 151, the spectrum resolution generally is not higher than 7 cm$^{-1}$, so that the spectrum resolution of the Raman spectrum imaging is limited. Therefore, in the present example, the light filtering apparatus 150 further includes a Fabry-Perot interference device, called as F-P interference device 152 for short hereinafter. The F-P interference device 152 is arranged between the narrow-band light filter 151 and the planar array detector 170. The Raman scattered light, after selectively passing through the narrow-band light filter 151, is incident on the F-P interference device 152 and further subjected to multi-beam interference effect of the F-P interference device 152, emerges from the F-P interference device 152 and is imaged on the planar array detector 170. Through the cooperative use of the F-P interference device 152 and the narrow-band light filter 151, the band-pass light filtering effect of ultra-narrow line width is realized within a large spectrum range, which is beneficial to obtaining more precise Raman spectrum information, and exerting the advantage of the fingerprint characteristic of the Raman spectrum.

In the present example, the F-P interference device 152 may be, but not limited to, one of air-gap F-P interference device 152, solid-gap F-P interference device 152, liquid-crystal tunable F-P interference device 152 and so on.

Figure 2:
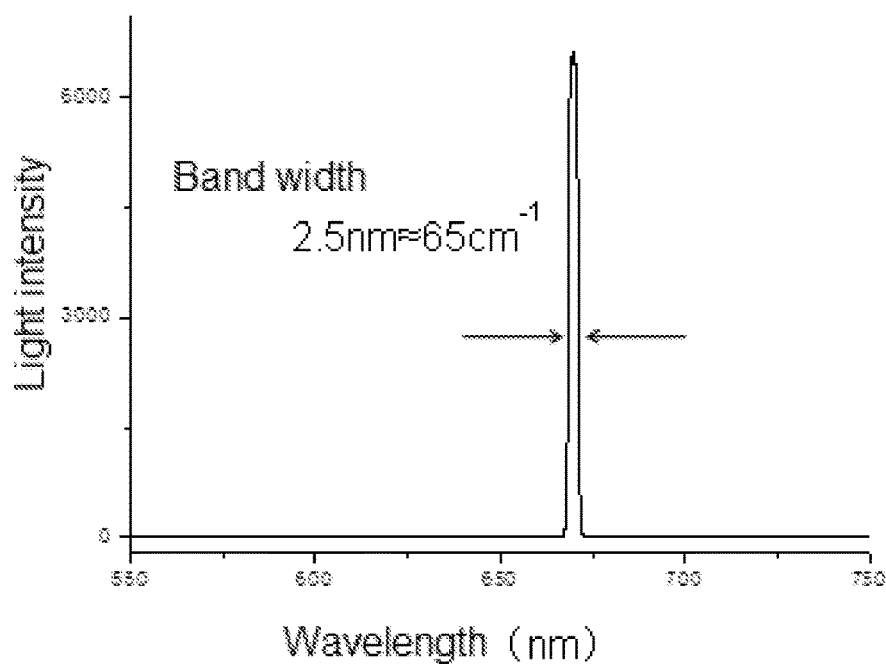
FIG. 2 is a schematic view of a transmission spectrum of a narrow-band light filter consistent with one or more aspects of the present disclosure.
Figure 3:
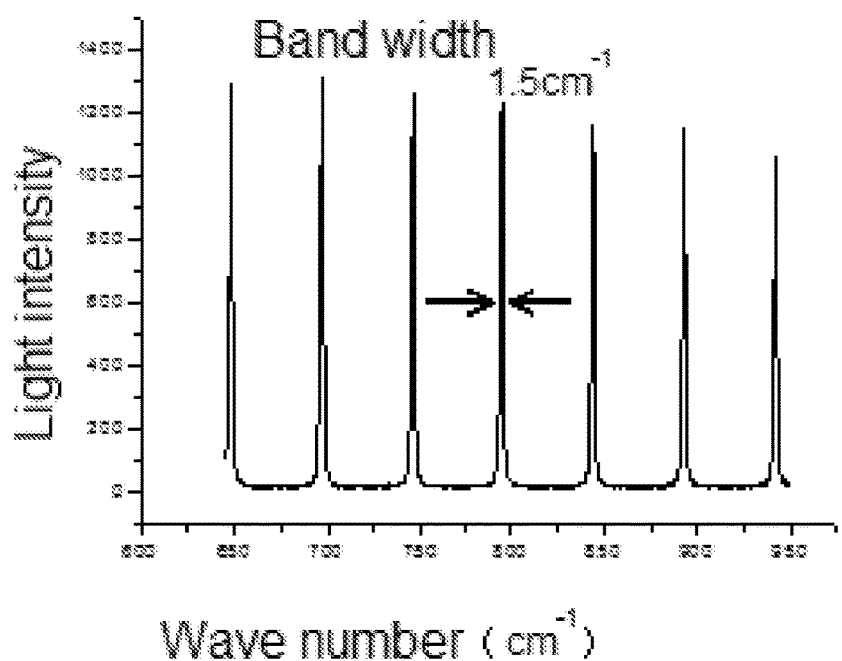
FIG. 3 is a schematic view of a transmission spectrum of an F-P interference device consistent with one or more aspects of the present disclosure.

As shown in FIG. 2, a transmission spectrum of the narrow-band light filter 151 includes one transmission peak having a certain band width. In FIG. 2, a horizontal axis represents wavelength, and a longitudinal axis represents light intensity. The transmission spectrum of the F-P interference device 152 includes a plurality of separate transmission peaks, forming a comb-like structure, as shown in FIG. 3. In FIG. 3, a horizontal axis represents wave number, and a longitudinal axis represents light intensity. A wavelength interval of two adjacent transmission peaks is just a free spectrum range of the F-P interference device 152. In order to obtain high spectrum resolution, an effort is made to ensure light with a single central wavelength to be transmitted as much as possible. In the present example, the free spectrum range of the F-P interference device 152 is larger than a half of the band-pass width of the band-pass light filter.

In order to enhance filtering-out of the Rayleigh scattered background light, the light filtering apparatus 150 may further include a long-pass light filter 153. The long-pass light filter 153 is arranged in a light path before the narrow-band light filter 151. At this time, the Raman scattered light generated by the sample 20 under the excitation of the laser light beams, after being incident on the light filtering apparatus 150, is specifically firstly incident on the long-pass light filter 153, then the light transmitted through the long-pass light filter 153 is incident on the narrow-band light filter 151, and the light transmitted through the narrow-band light filter 151 is further incident on the F-P interference device 152, emerges from the F-P interference device 152 and is imaged on the planar array detector 170.

The planar array detector 170 is used to convert a received optical image into an electrical signal, so as to obtain a Raman spectrum image. The Raman spectrum information may be further obtained according to the Raman spectrum image, so as to obtain the distribution situation of substances in the sample 20 corresponding to the Raman spectrum information. In the present example, the planar array detector 170 may be a conventional planar-array CCD (Charge-coupled Device), a planar-array electron-multiplying CCD (EMCCD), planar-array COMS (complementary metal oxide semiconductor) detector or planar-array intensified charge coupled device (ICCD), etc.

Below, parameter requirements of individual components of the Raman spectrum plane imaging device 10 provided in the present example will be explained taking one specific example. For example, in the Raman spectrum plane imaging device 10, the tunable laser device 111 is a continuous-wave dye laser device pumped by a YAG (yttrium-aluminum-garnet) laser device, which has an output power of 200-2000 mW and a wavelength adjustment range of 535-700 nm. It is assumed that the Raman spectrum imaging wavelength is fixed as 671 nm, that is, the central wavelength of the band-pass light filter is 671 nm. FIG. 2 shows a transmission spectrum of the narrow-band filtering apparatus. That is, the central wavelength of the light having Raman characteristic peak that may pass through the light filtering apparatus 150 is 671 nm. At this time, by tuning the output wavelength of the laser device, the Raman displacement selection and continuous scanning can be realized within a range of 200-2800 cm$^{-1}$. It is suitable for detecting Raman spectrum imaging of different substances without switching the light filter, and facilitates detection of the sample 20 having complex Raman spectra.

Correspondingly, a cut-off wavelength of the short-pass light filter 113 can be designed as 668 nm. The dichroscope 130 may have a reflecting wavelength less than 667 cm, and a transmission wavelength greater than 670 nm. The objective lens 140 is a 50-fold length-working-distance objective lens 140. The planar array detector 170 is an EMCCD. In the light filtering apparatus 150, the cut-off wavelength of the long-pass light filter 153 may be 668 nm.

Figure 4:
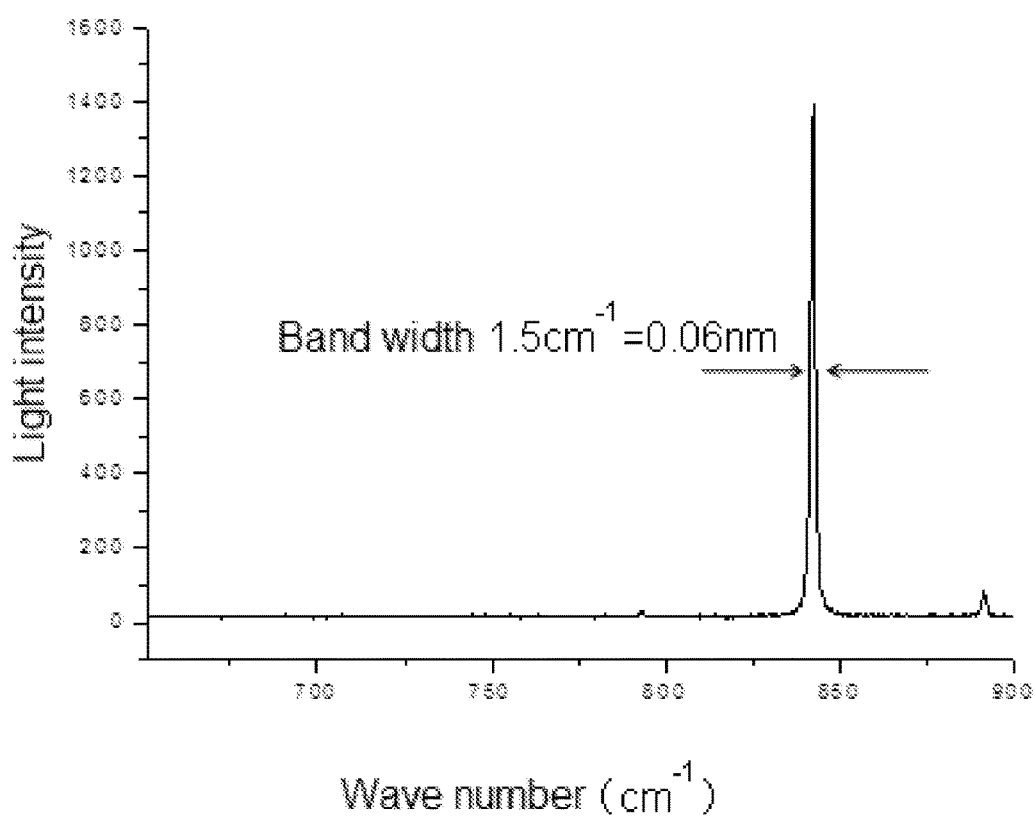
FIG. 4 is a schematic view of a transmission spectrum obtained when an F-P interference device and a narrow-band light filter are used in cooperation, according to one or more exemplary implementations of the present disclosure.

As shown in FIG. 2, the narrow-band light filter 151 has a central wavelength of 671 nm and a band-pass width of about 2.5 nm which is equivalent to approximately 65 cm$^{-1}$. Although the transmission efficiency is high, the band-pass width hardly satisfies the Raman spectrum imaging requirements. The F-P interference device 152 has an extremely high spectrum resolution, but its free spectrum range (wavelength interval between two interference peaks) is quite small, therefore, a specific F-P cavity needs to be designed so as to expand its free spectrum range. In the present example, a customized air-gap F-P interference device 152 is used, which, when used independently, has a transmission spectrum as shown in FIG. 3, in which the free spectrum range is relatively wide, being 1.3 nm, and the band-path width is 0.06 nm. When the F-P interference device 152 is used in cooperation with the narrow-band light filter 151, the band-pass light filtering effect of ultra-narrow line width can be realized within a large spectrum range, as shown in FIG. 4, in which a band-pass width of 1.5 cm$^{-1}$ can be achieved within a large spectrum range. In FIG. 4, a horizontal axis represents wave number, and a longitudinal axis represents light intensity. When a preceding-stage light filter of a narrower band-pass width and an F-P interference device 152 of higher fineness are used, a sub-wave-number spectrum resolution can be achieved, so that the Raman spectrum imaging of high spectrum resolution is realized, and theoretically, the spectrum resolution of higher than picometer can be achieved.

To sum up, in the Raman spectrum plane imaging device 10 provided in the examples of the present disclosure, the laser light beams output by the laser generation apparatus 110 irradiate on the preset region of the sample 20 in a planar illuminating manner, the generated Raman scattered light, after selectively passing through the light filtering device 150 based on spectra, is imaged on the planar array detector 170, to directly obtain the Raman spectrum image of the preset region of the surface of the sample 20. Use of such planar excitation and planar imaging manners effectively improves the imaging speed and the imaging spatial resolution of the Raman spectrum imaging. Besides, by adjusting the output wavelength of the laser generation apparatus 110, the Raman displacement selection and continuous scanning of the sample 20 can be realized without switching the light filtering apparatus 150, and the Raman spectrum plane imaging device is suitable for detecting the Raman spectrum imaging of different substances, and beneficial to detecting the sample 20 with complex Raman spectra.

The above are merely illustrative examples of the disclosed technology and should not be used to limit the presently-disclosed innovations. For one skilled in the art, various modifications and variations may be made to the present disclosure. Any modifications, equivalent replacements, improvements and so on, without departing from the spirit and principle of the present disclosure, should be covered by the scope of protection of the present disclosure.

What is claimed is:

1. A Raman spectrum plane imaging device, comprising:
a laser generation apparatus,
a light filtering apparatus, and
a planar array detector,
wherein laser light beams emitted by the laser generation apparatus irradiate on a preset region of a surface of a sample in a planar illuminating manner, and
wherein Raman scattered light, generated by the sample under excitation of the laser light beams and incident on the light filtering apparatus, selectively passes through the light filtering apparatus and is then imaged on the planar array detector, to be received by the planar array detector, wherein an output wavelength of the laser generation apparatus is adjustable,
wherein the Raman spectrum plane imaging device further comprises a dichroscope, wherein the laser light beams emitted by the laser generation apparatus are incident on the dichroscope and reflected by the dichroscope, and then irradiate on the preset region of the surface of the sample, and the Raman scattered light, which is generated by the sample under the excitation of the laser light beams, is incident on the dichroscope, transmitted through the dichroscope, and then incident on the light filtering apparatus.

2. The Raman spectrum plane imaging device according to claim 1, wherein the light filtering apparatus comprises a band-pass light filter and a Fabry-Perot interference device, wherein the Fabry-Perot interference device is provided between the band-pass light filter and the planar array detector, and the Raman scattered light, which is generated by the sample under the excitation of the laser light beams, is incident on the band-pass light filter, selectively passes through the band-pass light filter and incident on the Fabry-Perot interference device, emerges from the Fabry-Perot interference device and then is imaged on the planar array detector, wherein a free spectrum range of the Fabry-Perot interference device is larger than a half of a band-pass width of the band-pass light filter.

3. The Raman spectrum plane imaging device according to claim 2, wherein the band-pass light filter is a narrow-band light filter.

4. The Raman spectrum plane imaging device according to claim 3, wherein an incident angle of the Raman scattered light incident on the narrow-band light filter is adjustable.

5. The Raman spectrum plane imaging device according to claim 3, wherein the band-pass light filter is a band-pass light filter with a fixed central wavelength.

6. The Raman spectrum plane imaging device according to claim 3, wherein the light filtering apparatus further comprises a long-pass light filter, and the Raman scattered light, which is generated by the sample under the excitation of the laser light beams, passes through the long-pass light filter, the band-pass light filter, and the Fabry-Perot interference device in sequence, and then is imaged on the planar array detector.

7. The Raman spectrum plane imaging device according to claim 2, wherein the band-pass light filter is a band-pass light filter with a fixed central wavelength.

8. The Raman spectrum plane imaging device according to claim 2, wherein the light filtering apparatus further comprises a long-pass light filter, and the Raman scattered light, which is generated by the sample under the excitation of the laser light beams, passes through the long-pass light filter, the band-pass light filter, and the Fabry-Perot interference device in sequence, and then is imaged on the planar array detector.

9. The Raman spectrum plane imaging device according to claim 2, wherein the laser generation apparatus comprises a tunable laser device and a beam expander, wherein laser light beams emitted by the tunable laser device, after being expanded by the beam expander, irradiate on the surface of the sample, and the planar illuminating manner is a Kohler-type, critical-type or defocus-type planar illuminating manner.

10. The Raman spectrum plane imaging device according to claim 9, wherein the Raman spectrum plane imaging device further comprises a converging lens and an objective lens, and the laser light beams emitted by the tunable laser device, after being expanded by the beam expander, pass through the converging lens and the objective lens in sequence and then irradiate on the surface of the sample.

11. The Raman spectrum plane imaging device according to claim 2, wherein the output wavelength of the laser generation apparatus can be adjusted continuously.

12. The Raman spectrum plane imaging device according to claim 1, wherein the laser generation apparatus comprises a tunable laser device and a beam expander, wherein laser light beams emitted by the tunable laser device, after being expanded by the beam expander, irradiate on the surface of the sample, and the planar illuminating manner is a Kohler-type, critical-type or defocus-type planar illuminating manner.

13. The Raman spectrum plane imaging device according to claim 12, wherein the Raman spectrum plane imaging device further comprises a converging lens and an objective lens, and the laser light beams emitted by the tunable laser device, after being expanded by the beam expander, pass through the converging lens and the objective lens in sequence and then irradiate on the surface of the sample.

14. The Raman spectrum plane imaging device according to claim 1, wherein the output wavelength of the laser generation apparatus can be adjusted continuously.

* * * * *